(12) United States Patent
Wong et al.

(10) Patent No.: US 6,255,088 B1
(45) Date of Patent: Jul. 3, 2001

(54) ENZYMATIC SULFATION OF BIOMOLECULES

(75) Inventors: Chi-Huey Wong, Rancho Santa Fe, CA (US); Michael D. Burkart, Arlington, TX (US)

(73) Assignee: The Scripps Research Institute, La Jolla, CA (US)

( * ) Notice: Subject to any disclaimer, the term of this patent is extended or adjusted under 35 U.S.C. 154(b) by 0 days.

(21) Appl. No.: 09/393,013

(22) Filed: Sep. 10, 1999

Related U.S. Application Data
(60) Provisional application No. 60/133,565, filed on May 11, 1999.

(51) Int. Cl.$^7$ .............................. C12P 11/00; C12N 9/10; C12N 1/20; C12N 15/00

(52) U.S. Cl. ........................ 435/130; 435/101; 435/193; 435/257.3; 435/320.1; 536/23.2

(58) Field of Search .................................. 435/130, 101, 435/193, 252.3, 320.1; 536/23.2

(56) References Cited

PUBLICATIONS

Yang et al. Protein Expression and Purification, 8, 423–429 (1996).*
Saidha et al. Biochemical Journal 298: 45–50 (1994).*
Banerjee et al. B.B.A. 151 (1968) : 573–586. (1996).*
To, et al., "Rapid and Sensitive Assays Using High–Performance Liquid Chromatography to Measure the Activities of Phase II Drug Metabolishing Enzymes: Glucuronyl Transferase and Sulfotransferase", *J. Chromatog.* 301: 282–287(1984).
Stone, et al., "Kinetics of the Inhibition of Thrombin by Hirudin", *Biochemistry* 25 : 4622–4628 (1986).
Ramaswamy, et al., "Sulfotransferase Assay", *Methods Enzymol.* 143: 201–207 (1987).
Honkasalo, et al., "Determination of Phenol Sulphotransferase Activity by High Performance Liquid Chromatography", *J. Chromatog.* 424: 136–140 (1988).
Sim, et al., "Sensitive Assays for the Determination of Monoamine Oxidase and Phenol Sulphotransferase Activity in Small Tissue Samples", *J. Pharmacol. Methods* 24: 157–163 (1990).
Varin, et al., "Molecular Characterization of Two Plant Flavonol Sulfotransferases", *Proc. Natl. Acad. Sci. USA* 89: 1286–1290 (1992).
Chen, et al., "Tyrosine–Ester Sulfotransferase from Rat Liver: Bacterial Expression and Identification", *Protein Expression Purif.* 3: 421–426 (1992).
Nagata, et al., "Isolation and Expression of a cDNA Encoding a Male–Specific Rat Sulfotransferase that Catalyzes Activation of N–Hydroxy–2–acetylaminofluorene", *J. Biol. Chem.* 268: 24720–24725 (1993).

Schultze, et al., "In Vitro Sulfotransferase Activity of *Rhizobium meliloti* NodH protein: Lipochitooligosaccharide nodulation signals are sulfated after Synthesis of the Core Structure", *Proc. Natl. Acad. Sci. USA* 92: 2706–2709 (1995).
Kiehlbauch, et al., "Homodimeric and Heterodimeric Aryl Sulfotransferases Catalyze the Sulfuric Acid Esterification of N–Hydroxy–2–acetyl–aminofluorene", *J. Biol. Chem.* 270: 18941–18947 (1995).
Lin, et al., "Enzymatic Synthesis and Regeneration of 3'–Phosphoadenosine 5'–phosphosulfate (PAPS) for Regioselective Sulfation of Oligosaccharides", *J. Am. Chem. Soc.* 117: 8031–8032 (1995).
Hooper, et al., "From Legumes to Leukocytes: Biological Roles for Sulfated Carbohydrates", *FASEB J.* 10: 1137–1146 (1996).
Lin, et al., "Colorimetric Determination of the Purity of 3'–Phospho Adenosine 5'–Phosphosulfate and Natural Abundance of 3'–Phospho Adenosine 5'–Phosphate at Picomole Quantities", *Anal. Biochem.* 264: 111–117 (1998).
Falany, "Sulfation And Sulfotransferases: Introduction: Changing View of Sulfation and the Cytosolic Sulfotransferases", *FASEB J.* 11: 1–2 (1997).
Weinshilboum, et al., "Sulfation And Sulfotransferases 1: Sulfotransferase Molecular Biology: cDNA's and Genes", *FASEB J.* 11: 3–14 (1997).
Falany, "Sulfation And Sulfotransferases 3: Enzymology of Human Cytosolic Sulfotransferases", *FASEB J.* 11: 206–216 (1997).
Klaassen, et al., "Sulfation And Sulfotransferases 5: The Importance of 3'–Phosphoadenosine 5'–phosphosulfate (PAPS) in the Regulation of Sulfation", *FASEB J.* 11: 404–418 (1997).
Kakuta, et al., "The Sulfuryl Transfer Mechanism", *J. Biol. Chem.* 273: 27325–27330 (1998).
Bowman, et al., "Carbohydrate Sulfotransferases: Mediators of Extracellular Communication", *Chem. Biol.* 6: R9–R22 (1999).

\* cited by examiner

*Primary Examiner*—Ponnathapu Achutamurthy
*Assistant Examiner*—Tekchand Saidha
(74) *Attorney, Agent, or Firm*—Donald G. Lewis (57) ABSTRACT

Enzymatic sulfations of biomolecules catalyzed by 3'-phosphoadenosine-5'-phosphosulfate (PAPS) dependent sulfotransferases are enhanced by coupling the sulfation reaction an enzymatic regeneration of PAPS. The PAPS is enzymatically regenerated from its hydrolysis product 3',5'-diphosphate (PAP) using recombinant aryl sulfotransferase as the catalyst and aryl sulfate as the substrate. Biomolecules capable of enhanced sulfation by this method include carbohydrates, oligosaccharides, peptides, proteins, flavonoids, and steroids. When enzymatic sulfation and substrate regeneration steps are coupled, the desulfated aryl group produced in the regeneration step has a spectroscopic signature that can be employed for monitoring the progress of the sulfation of the biomolecule.

11 Claims, 7 Drawing Sheets

Figure 1

TABLE 1

| acceptor substrates | $K_{m, acceptor}$ (μM) | $k_{cat}$ (min$^{-1}$) |
|---|---|---|
| GlcNAcβ(1,4)GlcNAc | 243 ± 40 | 23.6 ± 1.7 |
| GlcNAcβ(1,4)GlcNAcβ(1,4)GlcNAc | 103 ± 12 | 27.5 ± 2.9 |
| GlcNAcβ(1,4)(GlcNAcβ(1,4))$_2$GlcNAc | 20.4 ± 3.6 | 19.7 ± 0.8 |
| GlcNAcβ(1,4)(GlcNAcβ(1,4))$_3$GlcNAc | 98.1 ± 12.4 | 25.9 ± 1.2 |
| GlcNAcβ(1,4)(GlcNAcβ(1,4))$_4$GlcNAc | 45.7 ± 6.0 | 22.7 ± 1.0 |
| Galβ(1,4)GlcNAc | 5575 ± 1057 | 8.0 ± 1.3 |
| Galβ(1,4)GlcNAcβ(1,3)Galβ(1,4)GlcNAc | 87.0 ± 6.3 | 3.4 ± 0.1 |

ENZYMATIC SULFATION OF BIOMOLECULES

This application claims the benefit of U.S. Provisional Application No. 60/133565, filed May 11, 1999.

TECHNICAL FIELD

The present invention relates to the preparative enzymatic synthesis of sulfated biomolecules. More particularly, the present invention relates to the preparative enzymatic synthesis of sulfated biomolecules including carbohydrates, oligosaccharides, peptides, proteins, flavonoids, and steroids and to xenobiotic sulfations. The present invention also relates to continuous assays for the spectrophotometric analysis of sulfotransferase reactions.

BACKGROUND

Sulfotransferases comprise a family of enzymes that catalyze the transfer of a sulfonate or sulfuryl group ($SO_3^{31}$) from the cofactor 3'-phosphoadenosine-5'-phosphosulfate (PAPS) (1) to an acceptor molecule. Even though it is more accurate to call these sulfonation reactions, the term sulfation is still widely used. The term sulfation will be employed within this specification with the understanding that a sulfonate or sulfuryl group is transferred. Sulfotransferases mediate sulfation of different classes of substrates such as carbohydrates, oligosaccharides, peptides, proteins, flavonoids, and steroids for a variety of biological functions including signaling and modulation of receptor binding (Bowman, K. G., et al., (1999) Chem. Biol. 6, R9–R22; and Falany, C. N., (1997) FASEB J. 11, 1–2). Within the past three years, many new sulfotransferases have been identified and cloned (Aikawa, J.-I., et al., (1999) J. Biol. Chem. 274, 2690; Dooley, T. P., (1998) Chemico-Biol. Interact. 109, 29; Fukuta, M., et al. (1998) Biochim. Biophys. Act. 1399, 57; Habuchi, H., et al. (1998) J. Biol. Chem. 273, 9208; Mazany, K. D., et al. (1998) Biochim. Biophys. Act. 1407, 92; Nastuk, M. A., et al. (1998) J. Neuroscience 18, 7167; Ong, E., et al., (1998) J. Biol. Chem. 273, 5190; Ouyang, Y.-B., et al., (1998) J. Biol. Chem. 273, 24770; Saeki, Y., et al. (1998) J. Biochem. 124, 55; Uchimura, K., et al. (1998) J. Biol. Chem. 273, 22577; and Yoshinari, K., et al., (1998) J. Biochem. 123, 740). A facile means to produce large amounts of sulfated product and efficient sulfotransferase assays are essential for the biological study of these enzymes and their sulfated products.

Sulfotransferases are the family of enzymes catalyzing sulfotransfer reactions, or the transfer of a sulfuryl group ($SO_3$) from 3'-phosphoadenosine-5'-phosophosulfate (PAPS) to an acceptor molecule. Sulfotransferases, present in most organisms and in all human tissues, mediate sulfation of different classes of acceptors for a variety of biological functions. To date, more than 30 sulfotransferase cDNAs have been isolated from animal, plant, and bacterial sources (Weinshilboum, R. M., et al. (1997) FASEB J. 11, 3–14). The varied and important roles sulfotransferases play in biological systems have only recently been uncovered, including detoxification, cell signaling, and modulation of receptor binding (Bowman, K. G., et al. (1999) Chem. Biol. 6, R9–R22; and Falany, C. N., (1997) FASEB J. 11, 206–216). Drug design to selectively inhibit these therapeutically important enzymes has quickly followed the discovery of their biological roles (Seah, V. M. Y., et al. (1994) Biochem. Pharmacol. 47, 1743–9; Bartzatt, R., et al. (1994) Biochem. Pharmacol. 47, 2087–95; Matsui, M., et al. (1995) Biochem. Pharmacol. 49, 739–41; Wong, C.-K., et al. (1997) Biochem. Biophys. Res. Commun. 233, 579–583; and Schuur, A. G., et al. (1998) Chem. Res. Toxicol. 11, 1075–1081). Given the monumental speed with which new sulfotransferases are being identified and interest in their synthetic application and the development of sulfotransferase inhibitors, simple and rapid activity assays are vital to the progress of this field.

PAPS, the universal sulfate donor and source of sulfate for all sulfotransferases, is a highly expensive and unstable molecule that has been an obstacle to the large-scale production of enzymatically sulfated products. The half-life of PAPS in aqueous solution at pH 8.0 is approximately 20 hours and is available from Sigma Co. Product inhibition by adenosine 3',5'-diphosphate (PAP) (3) has also been a limiting factor to large-scale applications. PAP inhibition of hydroxysteroid sulfotransferase was determined to be $K_i=14$ $\mu$M ( Marcus, D. J., et al. (1980) Aial. Biochem. 107, 296). PAP inhibits NodST with $K_i=0.1$ $\mu$M (Lin, C.-H., et al., (1995) J. Am. Cheni. Soc. 117, 8031).

SUMMARY

One aspect of the invention relates to an improved method for the preparative enzymatic sulfation of biomolecules, including carbohydrates, oligosaccharides, peptides, proteins, flavonoids, and steroids, and to xenobiotic sulfations, wherein the improvement is directed to the enzymatic regeneration of 3'-phosphoadenosine-5'- phosphosulfate (PAPS) from its byproduct 3',5'-diphosphate (PAP) using a recombinant aryl sulfotransferase and p-nitrophenyl sulfate. This regeneration system is more convenient than the existing methods for the kinetic analysis and synthetic application of sulfotransferases.

Accordingly, one aspect of the invention is directed to an improved sulfation process. The process is of a type wherein the sulfation of a biomolecule is catalyzed by a sulfotransferase with a conversion of 3'-phosphoadenosine-5'-phosphosulfate to adenosine 3',5'-diphosphate. The improvement is directed to the coupling of the sulfation process with an enzymatic regeneration of the 3'-phosphoadenosine-5'-phosphosulfate from the adenosine 3',5'-diphosphate. The enzymatic regeneration employs an arylsulfotransferase as the catalyst and an aryl sulfate as a substrate. Preferred biomolecules include carbohydrates, oligosaccharides, peptides, proteins, flavonoids, and steroids. The invention may also be employed to enhance xenobiotic sulfation reactions employing PAPS dependent sulfotransferases.

Another aspect of the invention is directed to a continuous spectrophotometric coupled-enzyme assay is employed for assaying sulfotransferase activity. This assay is based on the regeneration of 3'-phosphoadenosine-5'-phosphosulfate (PAPS) from the desulfated 3'-phosphoadenosine-5'-phosphate (PAP) by a recombinant aryl sulfotransferase using p-nitrophenyl sulfate as the sulfate donor and visible spectrophotometric indicator of enzyme turnover. Here recombinant rat aryl sulfotransferase IV (AST-IV) is expressed, resolved to the pure β-form during purification, and utilized for the regeneration. The activity of βAST-IV to catalyze the synthesis of PAPS from PAP and p-nitrophenyl sulfate is demonstrated via capillary zone electrophoresis, and the kinetics of this reverse-physiological reaction are calculated. βAST-IV is then applied to the coupled enzyme system, where the steady-state activity of the commercially available Nod factor sulfotranferase is verified with an enzyme concentration study and substrate-specificity assays of N-chitoses. The potential applications of this assay include rapid kinetic determinations for carbohydrate and protein sulfotransferases, high-throughput screening of potential sulfotransferase substrates and inhibitors, and biomedical screening of blood samples and other tissues for specific sulfotransferase enzyme activity and substrate concentration.

Accordingly, another aspect of the invention is directed to an assay for monitoring an enzymatic sulfation reaction. The enzymatic sulfation reaction is of the type which employs a conversion of 3'-phosphoadenosine-5'-phosphosulfate to adenosine 3',5'-diphosphate. The assay includes two steps. In the first step, the enzymatic sulfation reaction is coupled with an enzymatic regeneration of the adenosine 3',5'-diphosphate using an arylsulfotransferase in the presence of an aryl sulfate. Then, in the second step, the desulfation of the aryl sulfate is monotored spectroscopically and correlated with the enzymatic sulfation reaction of the first step.

Another aspect of the invention is directed to recombinant aryl sulfotransferase, including recombinant aryl sulfotransferase encoded by a plasmid contained in ATCC deposit accession number PTA-94.

BRIEF DESCRIPTION OF DRAWINGS

FIG. 2 is a table indicating the acceptor specificity for NodST with various substrates. The acceptor sugar concentrations were chosen around their respective $K_m$ values. The PAPS concentration was held constant at 20 $\mu$M. Kinetic constants were derived from the nonlinear, least-squares fit of the Michaelis-Menten equation with the LineWeaver program. Apparent kinetic values are indicated.

DETAILED DESCRIPTION

Enzymatic Sulfation of Biomolecules

Disclosed herein is an improved method for enzymatically sulfating biomolecules of a type which employs sulfotranferase as a catalyst and PAPS as a sulfuryl or sulfonate source, wherein the improvement is directed to the enzymatic regeneration of PAPS from PAP using recombinant aryl sulfotransferase IV (AST IV) and aryl sulfate. This enzyme, when coupled to a sulfotransferase of choice, transfers sulfate from p-nitrophenyl sulfate (2) to PAP. This system averts product inhibition by PAP while regenerating PAPS in situi and can be monitored quantitatively by measurement of the absorbance of released p-nitrophenol (4) at 400 nm. Additionally, this recycling system can be modified to serve as a continuous spectrophotometric assay for the activity of any sulfotransferase enzyme. The most common assay of sulfotransferase activity involves monitoring the transfer of radioisotopic sulfate from $^{35}$S-PAPS to the product, which is followed via thin-layer or paper chromatography using end-point methods (Ramaswamy, S. G., et al. (1987) *Methods Enzyniol.* 143, 201–7). These assays are expensive and often imprecise. $^{35}$S-PAPS is available from NEN Life Science Products. $^{35}$S half-life is 87.1 days. End-point methods of $^{35}$S detection of TLC normally involve indirect qualitative determination of radioactivity. Disclosed herein is the use of this one-enzyme PAPS regeneration system for the synthesis of N,N',N''-triacetylchitotriose 6-sulfate (5) and for a continuous, calorimetric, coupled-enzyme assay of NodST used to determine the substrate specificity of this enzyme.

The enzyme AST IV exists in two oxidative forms (Marshall, A. D., et al., (1997) *J. Biol. Chem.* 272, 9153–9160; Marshall, A. D., et al., (1998) *Chem. -Biol. Interact.* 109, 107–116; Yang, Y.-S., et al., (1998) *Chem. -Biol. Interact.* 109, 129–135; Yang, Y.-S., et al. (1996) *Protein Expression Purif.* 8, 423–429; Guo, W.-X. A., et al. (1994) *Chem.-Biol. Interact.* 92, 25–31; Chen, X., et al. (1992) *Protein Expression Purif.* 3, 421–6; Lin, E.-S., et al. (1998) *Anal. Biochem.* 264, 111–117; and Yang, Y.-S., et al., (1997) *Protein Eng.* 10, 70). These two oxidative forms can be easily resolved (Yang, Y.-S., et al. (1996) *Protein Expression Purif.* 8, 423–429), and the resolved physiologically relevant form has been utilized to assay picomole quantities of PAPS and PAP (Lin, E.-S, et al. (1998) *Anal. Biociheni.* 264, 111–117). As the bacterial expression of rat AST IV has been demonstrated (Chen, X., et al., (1992) *Protein Expression Purif.* 3, 421–6; and Ozawa, S., et al., (1990) *Nucleic Acids Res.* 18, 4001z.), AST IV was cloned from a rat liver cDNA library and overexpressed the enzyme in *E. coli.* AST IV gene obtained using polymerase chain reaction as described[3] (Yang, et al., 1996) from a cDNA library template provided by W. E. Balch lab, The Scripps Research Institute. The clone, containing an engineered NdeI site preceding the 5' coding region and a BamHI site following the3' stop codon, was digested with BamHI and NdeI and ligated with a similarly digested pET19b (Novagen, Madison, Wis.). The ligated plasmid was transformed into *E. coli* SURE (Stratagene, La Jolla, Calif.) for amplification. *E. coli* BL21 (DE3) (Novagen) were transformed with the amplified plasmid, and a single colony was chosen to innocluate 100 mL LB broth containing 50 $\mu$g/mL ampicillin. After overnight growth at 37° C., the culture was distributed into 4-1 L volumes of LB/ampicillin and grown at 37° to an $OD_{600}$ of 1.0. The cultures were induced with 50 $\mu$M IPTG, grown at 25° C. for 20 hours, and centrifuged. The cell pellet was resuspended in 100 mM Tris, pH 7.6, with 5 mM 2-mercaptoethanol and disrupted by French press. The supernatant was loaded onto a nickelagrose column and washed with a solution of 100 mM Tris, pH 7.6, 5 mM 2-mercaptoethanol, 300 mM NaCl, 5% glycerol, and 20 mM Imidazole followed by equilibration with 100 mM Tris, pH 9.0. 50 mM NaCl, and 5 mM BME. Alkaline phosphatase (500 U) was added and the resin was incubated at 20° C. for 15 hours. After washing the resin as above, β-form AST IV was eluted from the column with 100 mM Tris, pH 7.6 and 250 mM imidazole. Dialysis into 100 mM Tris pH 7.6, concentration, and dilution to 50% glycerol yielded 63 U (15.8 U/L) in 14 mL (4.5 U/ml) of glycerol stock. One unit is defined as 1 μmol of PAP is converted to PAPS per minute with p-nitrophenyl sulfate at pH 7.0. In order to obtain the pure β form of the enzyme in which PAP is not bound in the active site, conversion of the mixed enzyme forms was simply carried out during purification via nickel chromatography. The enzyme-bound nickel resin was incubated with alkaline phosphatase and β-mercaptoethanol prior to elution from the resin. The purified enzyme was then immediately available for PAPS regeneration. To distinguish the ability of AST IV to form PAPS from PAP and p-nitrophenyl sulfate rather than mere hydrolysis of p-nitrophenyl sulfate, capillary zone electrophoresis (CZE) was employed and verified the production of PAPS from PAP. CZE performed on BioRad 3000 with a coated 50 cm×50 μm ID capillary in 0.23 M borate, pH 7.8 running buffer, pressure injected 20 psi$^{-1}$sec, electrophoresis run 20.0 kV – to + at 20° C., detected at 260 nm. PAPS electroelutes at 5.53 minutes; PAP electroelutes at 5.98 minutes.

EXAMPLES

Methods

Capillary zone electrophoresis (CZE) was performed on BioRad 3000 with a coated 50 cm×50 μm ID capillary in 0.23 M borate in pH 7.8 running buffer. The sample was pressure injected at 20 psi$^{-1}$sec and electrophoresis was run with 20.0 kV (– to +) at 20° C. with detection at 260 nm. PAPS electroelutes at 5.53 min; PAP at 5.98 min.

AST IV gene was obtained using polymerase chain reaction as described (Yang, Y.-S., et al. (1996) *Protein Expression Purif* 8, 423–429) from a cDNA library template provided by W. E. Balch, The Scripps Research Institute. The clone, containing an engineered NdeI site preceding the 5' coding region and a BamHI site following the 3' stop codon, was digested with BamHI and NdeI and ligated with a similarly digested pET19b (Novagen, Madison, Wis.). The ligated plasmid was transformed into *E. coli* SURE (Stratagene, La Jolla, Calif.) for amplification. *E. coli* BL21 (DE3) (Novagen) were transformed with the amplified plasmid, and a single colony was chosen to innoculate 100 mL LB broth containing 50 μg mL$^{-1}$ ampicillin. After overnight growth at 37° C., the culture was distributed into 4 1 L volumes of LB/ampicillin and grown at 37° to an OD$_{600}$ of 1.0. The cultures were induced with 50 μM IPTG, grown at 25° C. for 20 hours, and centrifuged. The cell pellet was resuspended in 100 mM Tris, pH 7.6, with 5 mM 2-mercaptoethanol and disrupted by French press. The supernatant was loaded onto a nickel-agarose column and washed with a solution of 100 mM Tris, pH 7.6, 5 mM 2-mercaptoethanol, 300 mM NaCl, 5% glycerol, and 20 mM Imidazole followed by equilibration with 100 mM Tris, pH 9.0, 50 mM NaCl, and 5 mM BME. Alkaline phosphatase (500 U) was added and the resin was incubated at 20° C. for 15 hours. After washing the resin as above, β-form AST IV was eluted from the column with 100 mM Tris, pH 7.6 and 250 mM imidazole. Dialysis into 100 mM Tris pH 7.6, concentration, and dilution to 50% glycerol yielded 63 U (15.8 UL$^{-1}$) in 14 mL (4.5 U mL$^{-1}$) of glycerol stock. One unit is defined as 1 μmol of PAP converted to PAPS per minute with p-nitrophenyl sulfate at pH 7.0.

XLI-Blue MRF' *Escherichia coli* containing a DNA plasmid designated as pET19b-AST IV, obtained above, has been deposited with American Type Culture Collection (ATCC) on or before May 19, 1999 and has been assigned the ATCC accession number PTA-94. This deposit was made under the provisions of the Budapest Treaty on the International Recognition of the Deposit of Microorganisms for the Purpose of Patent Procedure and the Regulations thereunder (Budapest Treaty). This assures maintenance of a viable plasmid for 30 years from the date of each deposit. The plasmid will be made available by ATCC under the terms of the Budapest Treaty which assures permanent and unrestricted availability of the progeny of the plasmid to the public upon issuance of the pertinent U.S. patent or upon laying open to the public of any U.S. or foreign patent application, whichever comes first, and assures availability of the progeny to one determined by the U.S. Commissioner of Patents and Trademarks to be entitled thereto according to 35 U.S.C. §122 and the Commissioner's rules pursuant thereto (including 37 CFR §1.14 with particular reference to 886 OG 638). The assignee of the present application has agreed that if the plasmid deposit should die or be lost or destroyed when cultivated under suitable conditions, it will be promptly replaced on notification with a viable specimen of the same plasmid. Availability of the deposit is not to be construed as a license to practice the invention in contravention of the rights granted under the authority of any government in accordance with its patent laws.

N,N',N''-triacetylchitotniose 6-sulfate (5). N,N',N''-tniacetylchitotriose (314 mg, 500 μmol) in a 100 mL solution of bis-tris propane-HCl (100 mM, pH 7.0) with 5 mM dithiothreitol and 10 mM p-nitrophenyl sulfate, 11 mg PAP (25 μmol), 8.4 U NodST (Calbiochem, La Jolla, Calif.), and 18 U μ-AST IV were incubated at room temperature. Formation of N,N',N''-triacetylchitotriose 6-sulfate was monitored by TLC (7:1:2 n-propanol/30% NH$_4$OH/H$_2$O) and liberation of p-nitrophenol at 400 nm. After 3 days, the solution was passed through a column of LiChroPrep 18 (water). The void fraction was absorbed to a BioRad AG1-X8 column (HCO$_2$-form) and eluted with a linear gradient (0–0.1 M) of ammonium benzenesulfonate. Fractions containing N,N',N''-triacetylchitotriose 6-sulfate were concentrated and purified by size exclusion chromatography (BioGel P-2, water) to yield 207 mg (290 μmol, 58%) N,N',N''-triacetylchitotiose 6-sulfate. Positive ion electrospray MS (m/z) found N,N',N''-triacetychitotriose 6-sulfate, 730 [M+Na$^+$], as well as degradation product N,N',N''-triacetylchitotriose, 628 [M+H$^+$], 1-deoxy-N,N'-diacetylchitobiose, 407 [M$^+$], and 1-deoxy-N-acetylglucosamine, 204 [M$^+$]. For comparison, see original Nod signal characterization. HPLC: Two peaks (4.12, 4.37 min) correspond to α and β anomer of reducing end. A Waters Spherisorb S5 SAX column was used (4.6×250 mm) with 0.2 M→1.0 M NaCl linear gradient over 5 min in 10 mM KH$_2$PO$_4$ (pH 3.5), a flow rate of 1.0 mL min$^{-1}$, and detected at 220 nm. $^1$H NMR (500 MHz, D$_2$O): δ=4.25 (brd, 0.4 H, J=10.3 Hz, H6aβ), 4.20 (dd, 0.6 H, J=1.8, 11.0 Hz, H6aα), 4.16 (dd, 0.6 H, J=3.7, 11.0 Hz, H6bα), 4.12 (dd, 0.4 H, J=3.7, 9.6 Hz, H6bβ); $^{13}$C NMR (125 MHz, D$_2$O): δ=67.04 (C6α), 66.97 (C6β).

Assay of NodST 100 mM bis-tris propane-HCl, pH 7.0, 5 mM 2-mercaptoethanol, 20 μM PAPS, 2 mM p-nitrophenyl sulfate, 3.0 mU NodST, 6.4 mU β-AST IV, and substrate are combined to a total volume of 500 μL. Because commercial PAPS contains significant amounts of PAP, the assay solution is incubated for 30 minutes at 20° C. prior to addition of substrate. The evolution of p-nitrophenol is monitored at 400 nm for 10 minutes.

Enzymatic Sulfation of Carbohydrates and Oligosaccharides

Synthesis of N,N',N"-triacetylchitotriose 6-sulfate (207 mg) utilized commerically available NodST and the β-form of AST IV with 0.05 equivalents of PAP and 2.0 equivalents of p-nitrophenol sulfate in 58% yield. The structure was confirmed by electrospray degradation, HPLC (P. Lerouge, et al. *Nature,* 1990, 344, 781.), and NMR. Electrospray MS (positive mode) found N,N',N "-triacetychitotriose 6-sulfate (M+Na$^+$730) as well as degradation product N,N',N"-triacetylchitotriose (M+H$^+$628), 1-deoxy-N,N'-diacetylchitobiose (M$^+$407) and 1-deoxy-N-acetylglucosamine (M$^+$204). See original Nod signal characterization, Lerouge, P., et al., (1990) *Nature* 344, 781. Two HPLC peaks (4.12, 4.37 min) corresponding to α and β anomer of reducing end. Waters Spherisorb S5 SAX column (4.6×250 mm), 0.2 M→1.0 M NaCl liner gradient over 5 min in 10 mM KH$_2$PO$_4$ (pH 3.5) with a flow rate of 1.0 mL/min and detected at 220 nm. The same procedure was used in the synthesis of N,N',N",N'"-tetraacetylchitotetraose 6-sulfate on a 150 mg scale in 95% yield.

Figure 2:
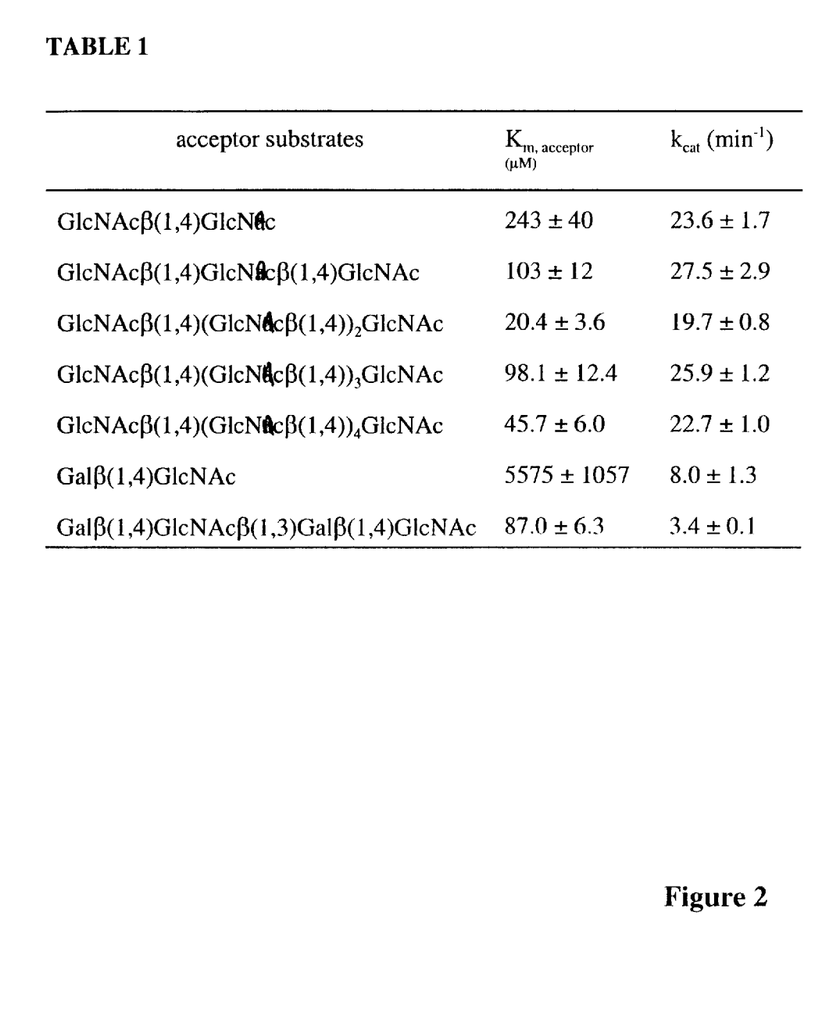
Figure 3:
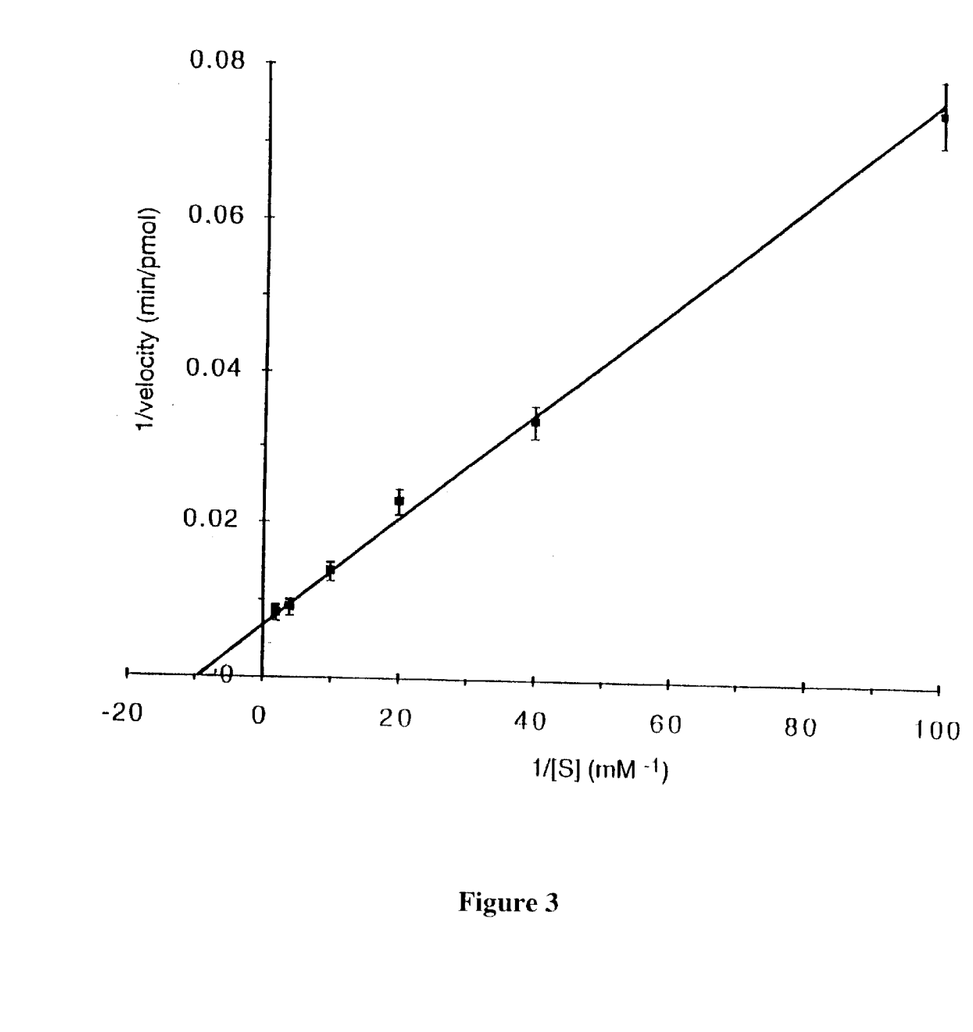
FIG. 3 illustrates a Lineweaver-Burke plot of kinetic data for N,N',N'',N'''-tetraacetyl-chitotetraose with NodST. ($K_m$=20.4±3.6 $\mu$M and $k_{cat}$=19.7±0.8 $min^{-1}$).
Figure 4:
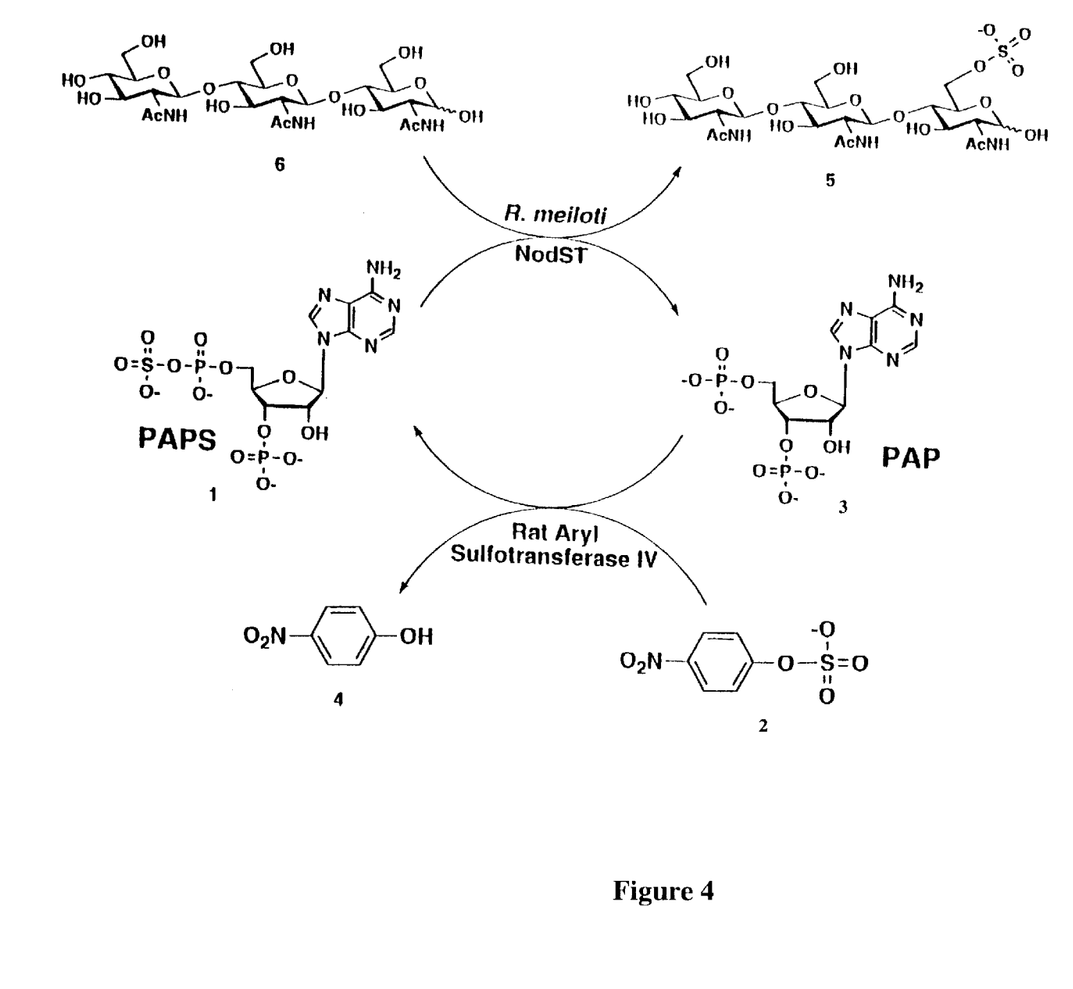
FIG. 4 illustrates an exemplary enzymatic sulfation of GlcNAcβ(1,4)GlcNacβ(1,4)-GlcNAc with the enzymatic regeneration of PAPS with β-aryl sulfotransferase IV and p-nitrophenyl sulfate.

The continuous assay for kinetic analysis of sulfotransferase enzymes resembles the large scale methodology with the exception that PAPS is added to the reaction in place of PAP, since the purpose of the assay is the continuous measurement of PAP production. The assay utilizes the β-form of AST IV described above. To demonstrate the application of this assay to the determination of enzymatic kinetic parameters, N,N',N'"-triacetylchitotriose at 10, 25, 50, 100, 250, and 500 mM was used as substrate. This data was fit to the Michaelis-Menten equation with the nonlinear, least squares program LineWeaver to yield a $K_m$=103 μM, $k_{cat}$=27.5 min$^{-1}$ (FIG. 3). LineWeaver is a graphical enzyme kinetics program for the Macintosh developed by Dr. Ian Ollmann at California Institute of Technology Acceptor sugar specificity experiments were also conducted to probe the substrate specificity of NodST with this assay. FIG. 2 contains the data for various N-acetyl chitoses, N-acetyllactosamine (LacNAc), and an N-acetyllactosamine dimer (Galβ(1,4)GlcNAcβ(1,3) Galβ(1,4)GlcNAc). Not surprisingly, N,N',N",N'"-tetraacetylchitotetraose proved to be the best substrate ($k_{cat}$=19.7 min$^{-1}$, $K_m$=20.4 μM), as it is the most similar to the natural substrate (Schultze, M., et al., (1995) *Proc. Natl. Acad. Sci. USA* 92, 2706–2709). Of particular interest is the sixty-fold increase in acceptor specificity from LacNAc to the LacNAc dimer. This assay can also be utilized for further studies of NodST substrate specificity and in application to large scale syntheses This new enzymatic regeneration of PAPS is disclosed to be highly practical and convenient for the synthesis of carbohydrate sulfates and kinetic analysis of sulfotransferases. This regeneration system is generally applicable to other PAPS dependent sulfotransferases. Several PAPS dependent enzyme catalyzed sulfations of oligosaccharides and carbohydrateds are disclosed by Bowman, K. G. et al., (Bowman, K. G., et al. (1999) *Chem. Biol.* 6, R9–R99). The performance and yield of all of the PAPS dependent enzyme catalyzed sulfations of oligosaccharides and carbohydrateds disclosed by Bowman can be enhanced by coupling such sulfation reactions with an enzymatic regeneration of PAP to reform PAPS, as disclosed herein.

Enzymatic Sulfation of Steroids

Enzyme catalyzed sulfation of steroids can also be enhanced by coupling PAPS dependent sulfation reactions with an enzymatic regeneration of the PAPS sulfuryl or sulfonate source. For example, the enzyme catalyzed sulfation of estradiol (an estrogen), as described by Kakuta, Y., et al., ( Kakuta, Y. et al., (1998) *J. Biol. Chern.* 273, 27325–27330), can enhanced by coupling the sulfation reaction with an enzymatic regeneration of the PAPS substrate. More particularly, estradiol (500 μmol) is combined in a 100 mL solution of bis-trispropane-HCl (100 mM, pH 7.0) with 5 mM dithiothreitol, 11 mg PAPS (25 μM), and 0.1 μg of mouse estrogen sulfotransferase, as adapted from the Kakuta reference, and then further combined with 18 U β-AST IV and 10 mM p-nitrophenyl sulfate for regenerating the PAPS. The resultant mixture is then incubated under reaction conditions at room temperature. The reaction may be monitored by HPLC or spectroscopically by the formation of 10 mM p-nitrophenol. After complete or substantial consumption of the starting material, the reaction is stopped and the mixture is lyophilized. The remaining solids may then be dissolved in a minimum amount of mobile phase and the mixture purified by preparative HPLC to obtain the sulfated product.

Enzymatic Sulfation of Flavonols and Flavonoids

Enzyme catalyzed sulfation of flavonols and flavonoids can also be enhanced by coupling PAPS dependent sulfation reactions with an enzymatic regeneration of the PAPS sulfuryl or sulfonate source. For example, the enzyme catalyzed sulfation of quercetin (a plant flavonol), as described by Varin, L., et al., (Varin, L., et al. (1992) *Proc. Natl. Acad. Sci.* 89, 1286–1290), can enhanced by coupling the sulfation reaction with an enzymatic regeneration of the PAPS substrate. More particularly, quercetin (500 μmol) is combined in a 100 mL solution of bis-trispropane-HCl (100 mM, pH 7.0) with 5 mM dithiothreitol, 11 mg PAPS (25 μM), and 0.1 μg of flavonol 3-sulfotransferase or flavonol 4'-sulfotransferase, as adapted from the Varin reference, and then further combined with 18 U β-AST IV and 10 mM p-nitrophenyl sulfate for regenerating the PAPS. The resultant mixture is then incubated under reaction conditions at room temperature. The reaction may be monitored by HPLC or spectroscopically by the formation of 10 mM p-nitrophenol. After complete or substantial consumption of the starting material, the reaction is stopped and the mixture is lyophilized. The remaining solids may then be dissolved in a minimum amount of mobile phase and the mixture purified by preparative HPLC to obtain the sulfated product.

Enzymatic Sulfation of Peptides and Proteins

Enzyme catalyzed sulfation of peptides and proteins can also be enhanced by coupling PAPS dependent sulfation reactions with an enzymatic regeneration of the PAPS sulfuryl or sulfonate source. For example, the enzyme catalyzed sulfation of hirudin (a potent anticoagulant protein secreted in the saliva of the medicinal leech), as described by Stone, S. R., et al. (Stone, S. R., et al. (1986) *Biochemistry* 25, 4622–4628), can enhanced by coupling the sulfation reaction with an enzymatic regeneration of the PAPS substrate. More particularly, hirudin (500 μmol) is combined in a 100 mL solution of bis-trispropane-HCl (100 mM, pH 7.0) with 5 mM dithiothreitol, 11 mg PAPS (25 μM), and 0.1 μg of tyrosylprotein sulfotransferase (TPST), as adapted from the Stone reference and then further combined with 18 U β-AST IV and 10 mM p-nitrophenyl sulfate for regenerating the PAPS. The resultant mixture is then incubated under reaction conditions at room temperature. The reaction may be monitored by HPLC or spectroscopically by the formation of 10 mM p-nitrophenol. After complete or substantial consumption of the starting material, the reaction is stopped and the mixture is lyophilized. The remaining solids may then be dissolved in a minimum amount of mobile phase and the mixture purified by preparative HPLC to obtain the sulfated product.

Xenobiotic Sulfations

Enzyme catalyzed xenobiotic sulfations can also be enhanced by coupling PAPS dependent sulfation reactions with an enzymatic regeneration of the PAPS sulfuryl or sulfonate source. For example, the enzyme catalyzed sulfation of N-hydroxy-2-acetylaminofluorene to form N-sulfonyloxy-2-acetylaminofluorene, as described by Nagata et al. (Nagata, k. et al., (1993) *J. Biol. Chem.* 268, 24720–24725), can enhanced by coupling the sulfation reaction with an enzymatic regeneration of the PAPS substrate. More particularly, N-hydroxy-2-acetylaminofluorene (106 mg, 500 µmol) is combined in a 100 mL solution of bis-trispropane-HCl (100 mM, pH 7.0) with 5 mM dithiothreitol, 11 mg PAPS (25 µM), and 0.1 µg of HAST I (N-hydroxyarylamine sulfotransferase), as described by the Nagata reference and then further combined with 18 U β-AST IV and 10 mM p-nitrophenyl sulfate for regenerating the PAPS. The resultant mixture is then incubated under reaction conditions at room temperature. The reaction may be monitored by HPLC or spectroscopically by the formation of 10 mM p-nitrophenol. After complete or substantial consumption of the starting material, the reaction is stopped and the mixture is lyophilized. The remaining solids may then be dissolved in a minimum amount of mobile phase and the mixture purified by preparative HPLC to obtain the sulfated product, according to the method of Kiehlbauch, C. C., et al. (Kiehlbauch, C. C., et al., (1995) *J. Biol. Chem.* 270, 18941–18947)

Assay for Sulfotransferase Activity

To date, the most common assay of sulfotransferase activity involves monitoring the transfer of radioisotopic sulfate from $^{35}$S-PAPS to the product, which is followed via thin-layer or paper chromatography using end-point methods (Ramaswamy, S. G., et al. (1987) *Methods Enzymol.* 143, 201–7). These assays are expensive, as $^{35}$S -PAPS is valued at around $1,000 per 100 µCi sample with a $^{35}$S half-life of 87.1 days. They are also imprecise end-point methods of $^{35}$S detection, usually via thin-layer silica or paper chromatography and involve indirect qualitative determination of radioactivity. Other reported sulfotransferase assays are also end-point analyses requiring other radioisotopes or rely on special fluorimetric properties of unique substrates (To, E.C.A., et al. (1984) *J. Chromatogr.* 301, 282–7; Honkasalo, T., et al. (1988) *J. Chromatogr.* 424, 136–40; and Sim, M. K., et al. (1990) *J. Pharmacol. Methods* 24, 157–63). A continuous, non-radioactive assay would be optimal for the routine estimation of kinetic constants of this important class of enzymes.

Figure 1:
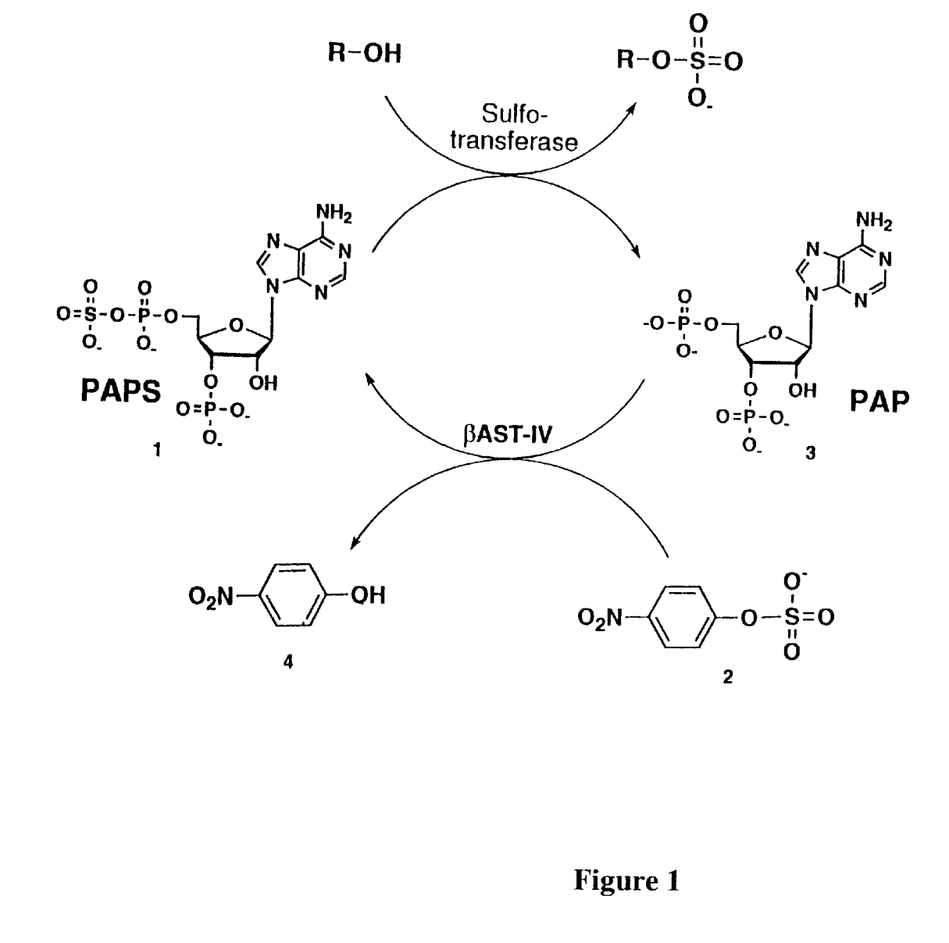
FIG. 1 illustrates a generalized scheme for the enzymatic sulfation of biomolecules with the enzymatic regeneration of PAPS with β-aryl sulfotransferase IV and p-nitrophenyl sulfate. The biomolecule, represented in FIG. 1 by R-OH, is of a type which includes a free hydroxyl moiety which is capable of enzyme catalyzed sulfation using PAPS as a sulfur source.

Disclosed herein is a continuous, coupled enzymatic assay for sulfotransferase activity that can be monitored simply by visible spectroscopy (FIG. 1). The assay relies upon the regeneration of PAPS (1) by recombinant aryl sulfotransferase IV (AST-IV), an enzyme cloned from rat liver cDNA that sulfates aryl alcohols from PAPS in vivo for the purpose of detoxification (Chen, X., et al. (1992) *Protein Expression Purif.* 3, 421–6). In this assay, AST-IV acts in the reverse-physiological direction with the addition of excess p-nitrophenyl sulfate (2) to regenerate PAPS from the desulfated 3'-phosphoadenosine-5'-phosphate (PAP) (3). AST-IV, the auxiliary enzyme in this coupled system, continuously regenerates each molecule of PAPS that has been converted to PAP by the primary enzymatic reaction. The use of p-nitrophenyl sulfate as sulfate donor provides the ability to monitor the coupled reaction calorimetrically due to the visible absorption of hydrolyzed p-nitrophenol (4) at 400 nm, obviating the common use of radioactivity for sulfotransferase monitoring. This assay also avoids enzyme product inhibition by PAP, demonstrated to inhibit sulfotransferases at low-micromolar levels (Marcus, C. J. S., et al. (1980) *Anal. Biochem.* 107, 296).

Recombinant AST-IV has been studied for many years, and important work has been published concerning the expression and purification (Chen, X., et al. (1992) *Protein Expression Purif* 3, 42–6; Guo, W.-X. A., et al. (1994) *Chem.-Biol. Interact.* 92, 25–31; and Lin, E.-S., et al. (1998) *Anal. Biochem.* 264, 111–117), acceptor specificity and inhibition (Rao, S. I., et al. (1991) *Drug Metab. Dispos.* 19, 543–5; Rao, S. I., et al. (1991) *Chirality* 3, 104–11; Duffel, M. W. (1994) *Chem.-Biol. Interact.* 92, 3–14; and Duffel, M. W., et al. (1993) *Drug Metab. Dispos.* 21, 400–2), and mechanism (Guo, W.-X. A., et al. (1994) *Chem. -Biol. Interact.* 92, 25–31; Yang, Y.-S., et al., (1996) *Protein Expression Purif.* 8, 423–429; Marshall, A. D., et al., (1998) *Chem. -Biol. Interact.* 109, 107–116; and Marshall, A. D., et al., (1997) *J. Biol. Chem.* 272, 9153–9160) of this enzyme. Recombinant AST-IV displays very good expression in *E. coli* and has been found to exist in two oxidative forms following expression. These two forms, αAST-IV and βAST-IV have markedly different binding affinities for PAP in the active site, displaying disparate reactivity and kinetics between the two forms (Yang, Y.-S., et al., (1996) *Protein Expression Purif.* 8, 423–429). These two oxidative forms are indicative of folding in the presence or absence of PAP, and they can be easily interconverted under the appropriate conditions. Recently Lin, et al. demonstrated that the resolved physiologically relevant form has been utilized to assay picomole quantities of PAPS and PAP (Lin, E.-S., et al. (1998) *Anal. Biochem.* 264, 111–117).

Also disclosed herein are the cloning, expression, and concomitant purification and oxidative resolution of βAST-IV. The enzyme is demonstrated to efficiently catalyze the reverse-physiological reaction, sulfating PAP with p-nitrophenyl sulfate to form PAPS, resulting in the chromogenic release of p-nitrophenol. This reaction is then coupled to a sulfotransferase of interest, here the commercially available Nod sulfotransferase (NodST) (Lin, C.-H., et al., (1995) *J. Am. Chem. Soc.* 117, 8031), to quantify activity. The utility of this assay is demonstrated for determining kinetic constants and substrate specificity information.

Materials and Methods

Materials

PAPS, N-acetyl-chito molecules, and NodST were purchased from Calbiochem (San Diego, Calif.). Rat liver cDNA library was purchased from Clonetech (Palo Alto, Calif.). Alkaline phosphatase was purchased from New England Biolabs (Beverly, Mass.). p-Nitrophenyl sulfate, PAP, and all other chemicals were purchased from Sigma (St. Luis, Mo.). The electrophoresis unit BioFocus 3000, buffers, and capillary were purchased from Bio-Rad (Richmond, Calif.). Capillary zone electrophoresis used a coated 50 cm×50 µm ID capillary with UV detection. The visible spectrometer DU-650 was purchased from Beckman instruments (Fullerton, Calif.).

Clonino and Expression of AST-IV

The AST-IV gene was obtained using polymerase chain reaction from a rat liver cDNA library. The clone, containing an engineered NdeI site preceding the 5' coding region and a BamHI site following the 3' stop codon, was digested with BamHI and NdeI and ligated with a similarly digested PET19b (Novagen, Madison, Wis.). The ligated plasmid was transformed into *E. coli* SURE (Stratagene, La Jolla, Calif.) for amplification. *E. coli* BL21(DE3) (Novagen) were transformed with the amplified plasmid, and a single colony was chosen to inoculate 100 mL LB broth containing 50 µg/mL ampicillin. After overnight growth at 37° C., the culture was distributed into 4-1 L volumes of LB/ampicillin and grown at 37° to an $OD_{600}$ of 1.0. The cultures were induced with 50 µM IPTG, grown at 25° C. for 20 hours, and centrifuged.

Purification and Oxidative Resolution to βAST-IV

Although the physiological sulfation of phenols by AST-IV has been carefully studied for two decades, the reverse-physiological catalysis of PAP to PAPS has not been the focus of AST-IV kinetic studies. This catalysis, introduced by Duffel, et al., is driven by a high concentration of p-nitrophenyl sulfate to form the high-energy PAPS product. It is disclosed herein that, in order to obtain reliable kinetic data from the reverse-physiological reaction, resolution of the two oxidative forms of AST-IV to the pure β-form is necessary. Yang, et al. demonstrated a stronger binding constant for PAP by purified αAST-IV over the β-form, in which PAP remains completely bound within the active site. They reported an absence of physiological activity (sulfation of phenols by PAPS) by the isolated a-form, presumably due to the tight-binding of PAP. However, it is disclosed herein that both forms catalyze the reverse-physiological reaction. If the enzyme is used in mixed α/β form, the detected velocity of the reverse-physiological reaction appears as the sum of the velocities contributed by each (Segal, I. H. (1975) in Enzyme Kinetics, pp. 64–71, John Wiley and Sons, Inc., New York)

$$V=(Vmax_1[S])/(Km_1+[S])+(Vmax_2[S])/(Km_2+[S])$$

and displays kinetics indicative of catalysis by two-enzymes. This phenomenon also occurs when the mixed enzymes are used in a coupled system, yielding non-specific kinetic data. Only after resolution to the single β-form were linear double-reciprocal plots observed.

Resolution to the β-form is simply carried out by incubation in 5 mM β-mercaptoethanol in the presence of alkaline phosphatase at pH 9.0. It is disclosed herein that this resolution can be easily incorporated into the purification process. Having cloned AST-IV as a histidine-tagged fusion protein, purification via nickel agarose follows cell lysis. The resin with bound enzyme is equilibrated with alkaline phosphatase buffer at pH 9.0, and 500 U alkaline phosphatase is added. Incubation of the resin overnight followed by washing the resin and standard elution from the nickel column to provide purified βAST-IV with a production yield of 15.8 U/L.

The cell pellet was resuspended in 100 mM Tris, pH 7.6, with 5 mM β-mercaptoethanol and disrupted by French press. The supernatant was loaded onto a nickel-agarose column and washed with a solution of 100 mM Tris, pH 7.6, 5 mM 2-mercaptoethanol, 300 mM NagCl, 5% glycerol, and 20 mM Imidazole followed by equilibration with 100 mM Tris, pH 9.0, 50 mM NaCl, and 5 mM β-mercaptoethanol. Alkaline phosphatase (500 U) was added, and the resin was incubated at 20° C. for 15 hours. After washing the resin again as above, βAST-IV was eluted from the column with 100 mM Tris, pH 7.6 and 250 mM imidazole. Dialysis into 100 mM Tris pH 7.6, concentration, and dilution to 50% glycerol yielded 63 U (15.8 U/L) in 14 mL (4.5 U/ml) of glycerol stock. One unit is defined as 1 µmol of PAP converted to PAPS per minute with p-nitrophenyl sulfate at pH 7.0.

Detection of PAPS Production by Capillary Zone Electrophoresis

Figure 5:
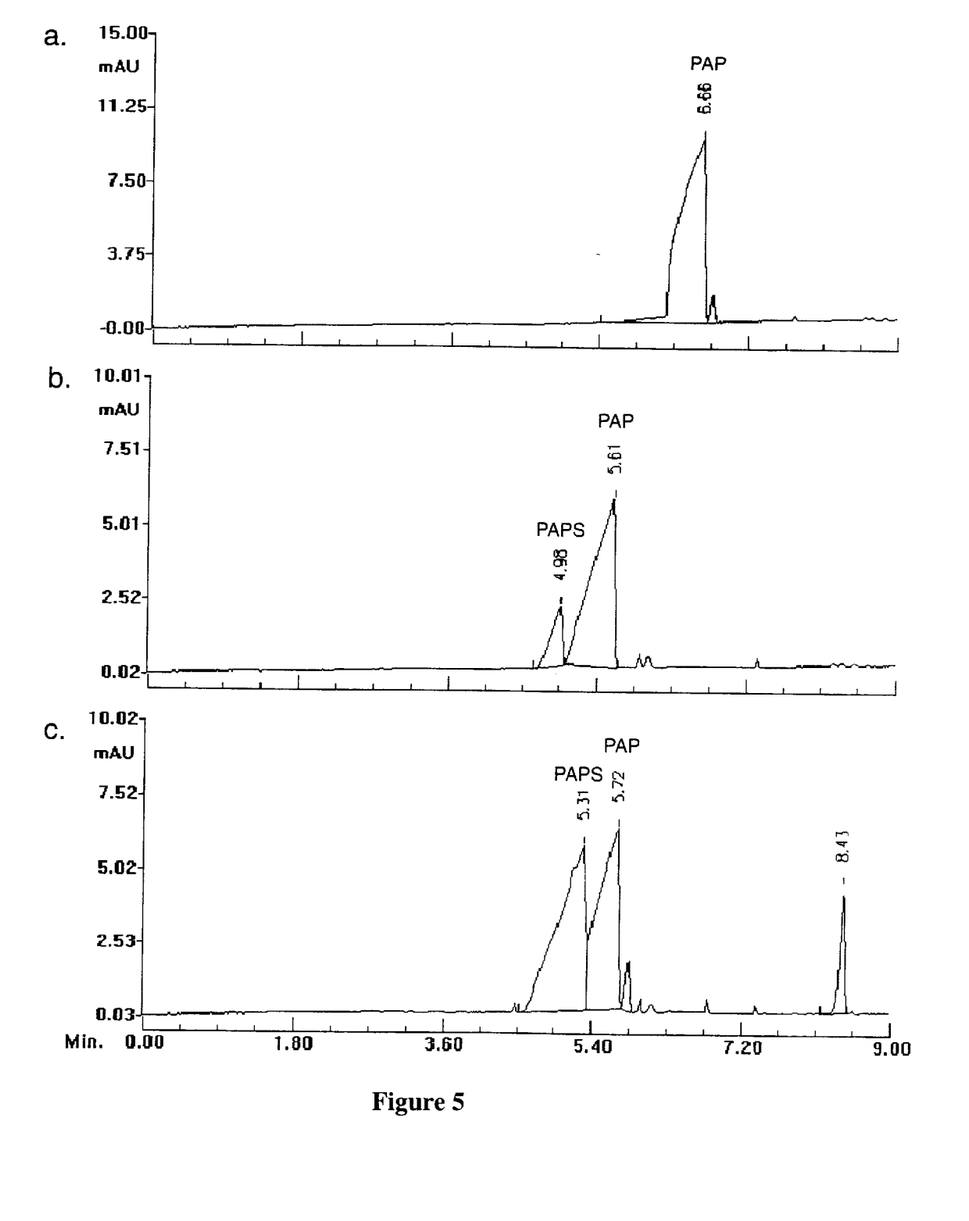
FIG. 5 illustrates capillary zone electrophoresis measurements. a) Before addition of enzyme, one peak corresponds to PAP. b) 30 minutes after addition of βAST-IV, a new peak at 4.98 min. is detected. c) Addition of 40 $\mu$M PAPS as an internal standard verifies enzymatic production of PAPS. Other peaks are impurities present in commercial PAPS.

To differentiate reverse-physiological catalysis instead of mere p-nitrophenyl sulfate hydrolysis, CZE was conducted to identify formation of PAPS (FIG. 5.). A standard sample containing 1 mM each of PAPS, PAP, and 3'-AMP was first subjected to CZE to determine relative retention times. The reverse-physiological assay was analyzed before addition of βAST-IV to colrelate PAP with the standard sample (a.). A single peak is detected, indicating that only PAP is present prior to addition of enzyme. 30 minutes after initiation by βAST-IV, CZE was repeated. A new peak is seen, indicative of PAPS formation by the enzyme (b.). The elution-time of PAP has been altered due to addition of the enzyme and the buffers present in the enzyme solution. Dilution during addition of the enzyme results in decrease of signal intensity. To demonstrate that the new peak was that of PAPS, addition of an internal PAPS standard (40 µM final concentration) verified that the new peak is indeed PAPS (c.). Elution times have again been slightly altered, this time by addition of the PAPS standard. The new peaks seen in c. represent impurities present in commercially available PAPS, probably corresponding to ATP or ADP.

All capillary zone electrophoresis (CZE) was run in 0.23 M borate in running buffer at pH 7.8. The column was pre-washed with $H_2O$ (1 min), 1 N NaOH (1 min), and running buffer (2 min). The sample was pressure injected at 20 psi sec and electrophoresis was run with 20.0 kV (– to +) at 20° C. with detection at 260 nm. CZE of 1 mM standards PAPS, PAP, and 3'-adenosine monophosphate (3'-AMP) were run to determine retention times. The reverse-physiological reaction assay mixture, a 500 µL solution containing 50 mM bis-tris propane-HCl buffer at pH 7.0, 1 mM 2-mercaptoethanol, 10 mM p-nitrophenyl sulfate, and 1 mM PAP at 25° C., was subjected to CZE prior to addition of enzyme (t=0). 5 mU βAST-IV was added and CZE was repeated 30 minutes after initiation. The reaction was then diluted 100-fold and CZE was run again. A 2.0 µL internal standard of 10 mM PAPS was added, and CZE was repeated.

Quantification of Reverse-physioloical Catalysis with µAST-IV

Figure 6:
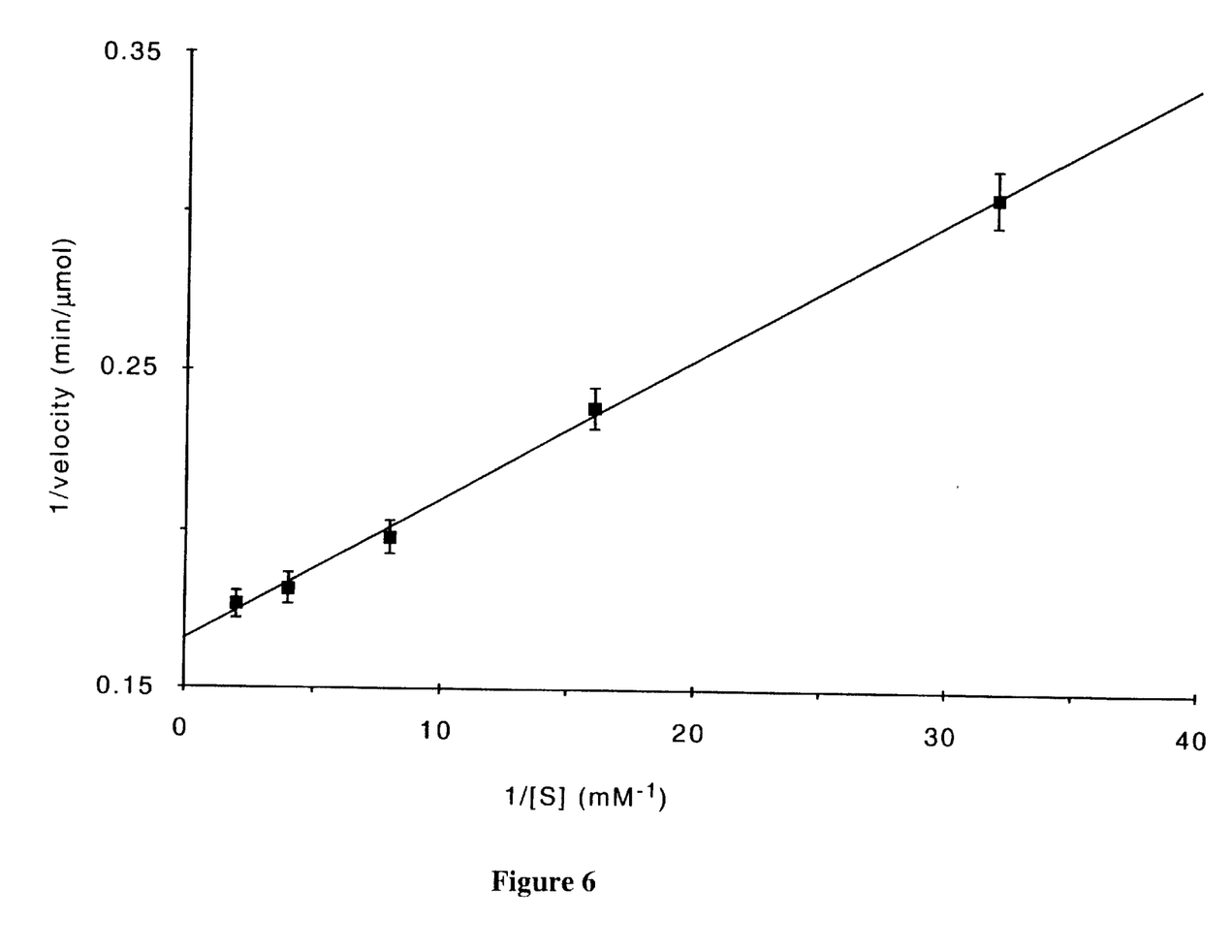
FIG. 6 illustrates the initial velocity of $\mu$AST IV catalysis of PAPS from PAP and p-nitrophenyl sulfate as a function of the concentration of PAP. $K_m$=26.4±3.4 $\mu$M, $V_{max}$=6.04±0.24 $\mu$mol/min.

To demonstrate true first-order Michaelis-Menten kinetics, the apparent $K_m$ and $V_{max}$ of βAST-IV was determined as a function of PAP concentration. FIG. 6 shows the linear double reciprocal Lineweaver-Burk plot indicating first-order rate kinetics in the reverse-physiological direction, giving $K_m$=26.4±3.4 mM and $V_{max}$=6.04±0.24 µmol/min, similar to published values from the forward physiological reaction (Marshall, A. D., et al., (1997) *J. Biol. Cheem.* 272, 9153–9160).

βAST-IV activity in the reverse-physiological reaction was determined at 25° C. with a total volume of 500 µL. The reverse-physiological assay above was used with varying PAP concentration (15.6, 31.3, 62.5, 125, 250, 500 µM). Measurement of initial velocity was conducted over 10 seconds at 400 nm, and an extinction coefficient of 1064 was used to calculate p-nitrophenol concentration at pH 7.0. $K_m$ and $V_{max}$ calculations were made with the LineWeaver enzyme kinetics program for Macintosh (Ian Ollmann, Pasadena, Calif.).

Figure 7:
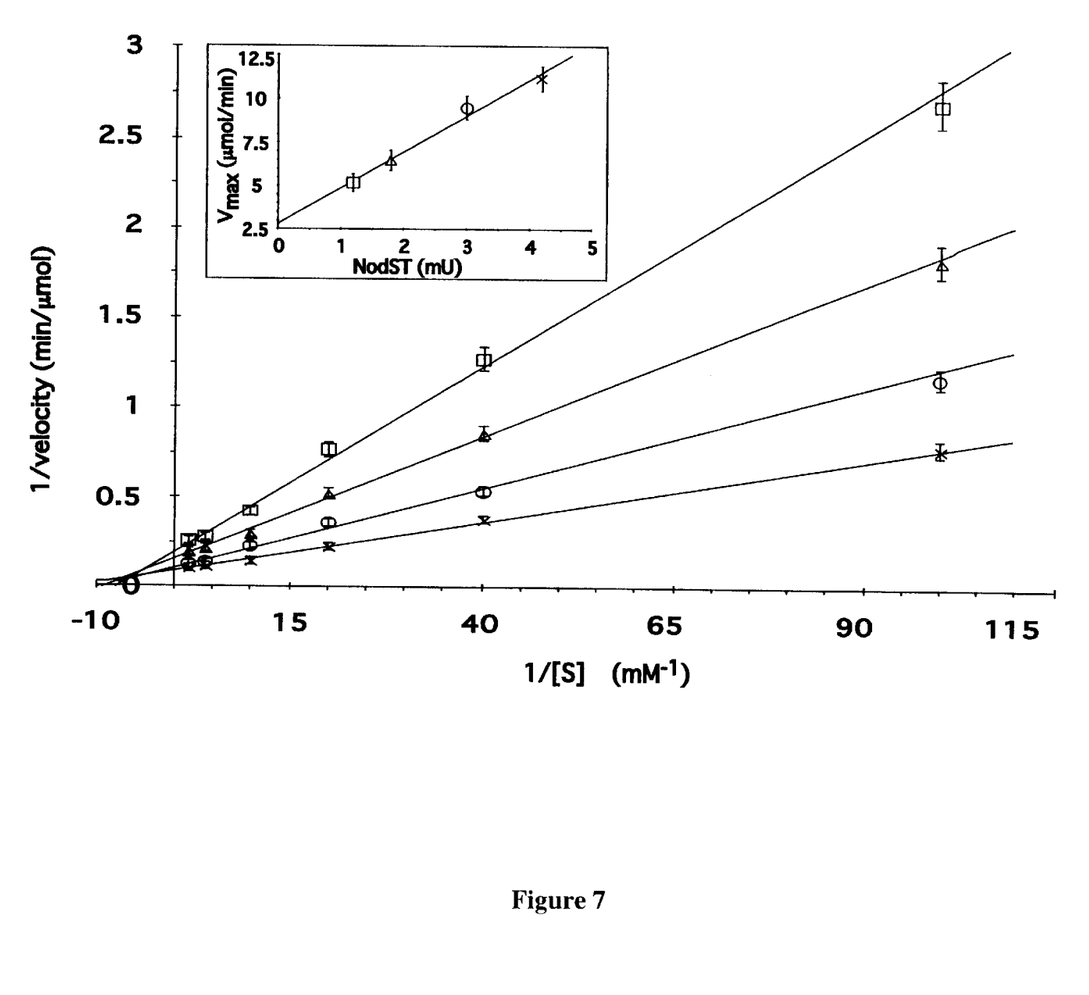
FIG. 7 illustrates the results of a coupled assay for providing accurate initial velocity kinetic determinations with the sulfation of N,N',N''-triacetylchitotriose. The concentration of the primary enzyme, NodST, is varied (□−1.2 mU, Δ−1.8 mU, ○−3.0 mU, X−4.2 mU) and represented in a double-reciprocal (1/v vs. 1/[s]) Lineweaver-Burk plot. Insert: A linear relationship is observed with $V_{max}$ plotted as a function of enzyme concentration.

Coupled Sulfotransferase Assay Conditions; Enzyme Concentration Study of NodST Activity For a valid coupled assay system, the auxiliary enzyme must convert the initial product at a rate fast enough to monitor the steady-state production of the initial product and not the rate of the auxiliary enzyme (Rudolph, F. B., et al., (1979) *Methods Enzymol.* 63, 22–43). To ensure this, initial substrates must be saturating, and the auxiliary reaction must be irreversible and first-order with respect to the initial product. The first condition can be simply regulated by careful substrate and enzyme concentrations. Two factors ensure the second condition in this coupling system. The first is the use of a saturating amount of p-nitrophenyl sulfate, and the second is the fortuitous fact that the auxiliary enzyme (βAST-IV) converts the initial product (PAP) back into the substrate (PAPS) for the first enzyme, ensuring continuous saturating conditions. Additionally, removal of PAP avoids product inhibition of the primary enzyme. Hence, the major requirements of this assay are a saturating amount of p-nitrophenyl sulfate, a PAPS concentration much greater than the $K_m$, for the first enzyme, and an excess of βAST-IV activity (catalysis of PAPS formation) with respect to the first enzyme (degradation of PAPS).

βAST-IV was chosen to couple in the reverse-physiological reaction to recombinant Nod factor sulfotransferase (NodST), a commercially available sulfotransferase that is responsible for the in vivo sulfation of a lipid-linked N,N',N",N"'-tetraacetylchitotetraose in *Rhizobium melioti* for legume nodulation (Lerouge, P., et al., (1990) *Nature* 344, 781–782). NodST also catalyzes the sulfation of various N-acetyl-chitose oligosaccharides in vitro. (Lin, C.-H., et al., (1995) *J. Am. Chem. Soc.* 117, 8031; and Schultze, M., et al., (1995) *Proc. Natl. Acad. Sci. USA* 92, 2706–2709) The first proof of a valid coupled enzyme system was the enzyme concentration study of NodST. Here the concentration of NodST was varied (1.2, 1.8, 3.0, and 4.2 mU/reaction), and the initial velocity data was used to determine $K_m$ and $V_{max}$ values. True Michaelis-Menten steady-state kinetics will yield equal $K_m$ values, and $V_{max}$ will vary in a linear manner vs. enzyme concentration. FIG. 7 demonstrates this experiment in which the coupled system indeed yields near exact $K_m$ values and $V_{max}$ (FIG. 7, inset) proves linear with respect to βAST-IV concentration.

All reactions were run in a total volume of 500 μL at 25° C. Each monitored reaction contained 100 mM bis-tris propane-HCl, pH 7.0, 5 mM 2-mercaptoethanol, 20 μM PAPS, 2 mM p-nitrophenyl sulfate, 6.4 mU βAST-IV, and varied concentrations of N,N',N"-triacetylchitotriose (10, 25, 50, 100, 250, and 500 μM). The amount of NodST added to each series of acceptor concentrations is varied over 1.2, 1.8, 3.0, and 4.2 mU. Because commercial PAPS contains significant amounts of PAP, the assay solution is incubated for 30 minutes at 20° C. prior to addition of substrate. The evolution of p-nitrophenol is monitored at 400 nm for 10 minutes.

PAPS Concentration Study of Coupled NodST Assay

Although the precise $K_m$ of NodST for PAPS has not been reported, our preliminary study indicated that it is <0.1 μM Indeed, most sulfotransferases demonstrate sub-micromolar $K_m$ values for PAPS. To ensure that our coupled assay provides a steady-state PAPS concentration that is much greater than the $K_m$ of NodST, the $K_m$ experiments above were conducted with varying concentrations of PAPS to verify PAPS saturation. Three $K_m$-determination experiments for N,N',N"-triacetylchitotriose were run at 20, 40, and 100 μM PAPS concentrations. It was found that all three experiments yielded $K_m$ and $k_{cat}$ values within 10% variation of $K_m$=243 μM and $k_{cat}$=23.6 s$^{-1}$. A previously published study using a radioisotopic thin-layer chromatography method to determine kinetic values of NodST maintained 100 μM PAPS concentration for all assays. Given that AST-IV maintains a constant concentration of PAPS through recycling, it is disclosed that 20 μM PAPS reaction concentration is sufficient for saturation conditions to maintain steady-state.

Three series of reactions with varying concentrations of PAPS (20, 40, and 100 μM) were run in the above coupled assay conditions and used to determine $K_m$ of N,N',N"-triacetylchitotriose in each case. Each series was varied in concentration of N,N',N"-triacetylchitotriose from 10 to 500 μM, as above. 3.0 mU of NodST was used in each reaction. The $K_m$ for each series of PAP concentrations was calculated and the values were compared.

Determination of Acceptor Specificity for NodST

Although the natural substrate of NodST has been identified and several substrates have been demonstrated (Lin, C.-H., et al., (1995) *J. Am. Chem. Soc.* 117, 8031), the exact kinetic constants for most sulfate acceptors have not been published. FIG. 2 contains $K_m$, $k_{cat}$, and $V_{max}$ values for all five N-acetylchitoses, N,N'-diacetylchitobiose, N,N',N"-triacetylchitotriose, N,N',N",N"'-tetraacetylchitotetraose, N,N',N",N"',N""-pentaacetylchito-pentaose, and N,N',N", N"',N"",N"""-hexaacetylchitohexaose. From this data, the tetramer proves to be the best substrate, indicating that it is most closely related to the natural tetrameric substrate.

These results compare favorably to published $K_m$ values determined by a non-coupled, radioisotope thin-layer chromatography assay. Although, not all of these substrates were previously tested, N,N',N",N"'-tetraacetylchitotetraose and N,N',N",N"',N""-pentaacetylchito-pentaose were reported to yield $K_m$ values of 140 μM and 190 μM, respectively. This coupled assay method determined these values to be 20.4 μM and 98.1 μμM, respectively. The discrepancy between these values may be due to the inherent inaccuracy of the radioisotopic thin-layer chromatography assay. This coupled system allows the continuous measurement of initial reaction velocity more accurately than stop-time assays.

This coupled sulfotransferase system is useful for the kinetic analysis and synthetic application of sulfotransferase enzymes and can also aid the search for new sulfotransferase-inhibiting molecules. Clearly, any inhibitor studied with this system would require specificity to the primary enzyme rather than having broad sulfotransferase activity. Similarly, enzymes studied with this coupled system must not have cross-reactivity with βAST-IV substrates. This assay may also be directed applied to the kinetic study of carbohydrate or protein sulfotransferases, two classes of sulfotransferase enzymes, which are currently very active areas of new enzyme discovery and drug design. This assay is also applicable to high-throughput screening of potential sulfotransferase substrates and inhibitors. With the emergence of parallel and combinatorial chemistry in drug discovery, a simple, non-radioactive screening assay such as this is essential to the discovery process. This assay can also be employed in biomedical analyses of blood and tissues for sulfotransferase enzymes and metabolic substrates. Recent implications of the role of carbohydrate sulfation in diseases such as chronic inflammation, cancer metastasis, cartilage formation, and hoimone regulation indicate a future need for rapid biomedical analysis. (Bowman, K. G., et al. (1999) *Chem. Biol.* 6, R9–R99).

What is claimed is:

1. An improved sulfation process, the process being of a type wherein the sulfation of a biomolecule or xenobiotic molecule is catalyzed by a first sulfotransferase with a conversion of 3'-phosphoadenosine-5'-phosphosulfate to adenosine 3',5'-diphosphate, wherein the improvement comprises:

coupling said sulfation process with an enzymatic regeneration of the 3'-phosphoadenosine-5'-phosphosulfate from the adenosine 3',5'-diphosphate, said enzymatic regeneration being catalyzed by a second sulfotransferase, said second sulfotransferase being an arylsulfotransferase, said second sulfotrasferase employing an aryl sulfate as a substrate, said first and second sulfotransferases being not identical.

2. An improved sulfation process as described in claim 1 wherein the biomolecule is selected from a group consisting of carbohydrates, oligosaccharides, peptides or proteins, flavonoids, and steroids.

3. An improved sulfation process as described in claim 2 wherein the substrate is an oligosaccharide.

4. An improved sulfation process as described in claim 2 wherein the substrate is a carbohydrate.

5. An improved sulfation process as described in claim 2 wherein the substrate is a peptide.

6. An improved sulfation process as described in claim 2 wherein the substrate is a protein.

7. An improved sulfation process as described in claim 2 wherein the substrate is a flavonoid.

8. An improved sulfation process as described in claim 2 wherein the substrate is a steroid.

9. An improved sulfation process as described in claim 1 wherein the biomolecule or xenobiotic molecule is a carbohydrate, the aryl sulfotransferase is a recombinant aryl sulfotransferase, and the aryl sulfate is p-nitrophenyl sulfate.

10. An improved sulfation process as described in claim 1 wherein the substrate is xenobiotic.

11. An assay for monitoring an enzymatic sulfation reaction of a biomolecule or a xenobiotic molecule employing a first sulfotransferase with a conversion of 3'-phosphoadenosine-5'-phosphosulfate to adenosine 3',5'-diphosphate, said assay comprising the following steps:

Step A: coupling said enzymatic sulfation reaction of the biomolecule or the xenobiotic molecule with an enzymatic regeneration of the adenosine 3',5'-diphosphate using a second sulfotransferase, said second sulfotransferase being an arylsulfotransferase in the presence of an aryl sulfate; and then Step B: spectrophotometrically monitoring a desulfation of the aryl sulfate and correlating said desulfation with a quantification of the enzymatic sulfation of the biomolecule or xenobiotic molecule in said Step A.

* * * * *

UNITED STATES PATENT AND TRADEMARK OFFICE
CERTIFICATE OF CORRECTION

| | |
|---|---|
| PATENT NO. | : 6,255,088 B1 |
| DATED | : July 3, 2001 |
| INVENTOR(S) | : Wong et al. |

It is certified that error appears in the above-identified patent and that said Letters Patent is hereby corrected as shown below:

<u>Column 1,</u>
Line 4, insert -- This invention was made with government support under Contract No. GH44154 by the National Institutes of Health. The government has certain rights in the invention. --

Signed and Sealed this

Fifth Day of March, 2002

*Attest:*

*Attesting Officer*

JAMES E. ROGAN
*Director of the United States Patent and Trademark Office*